United States Patent
Chanin

(10) Patent No.: US 10,447,906 B2
(45) Date of Patent: Oct. 15, 2019

(54) DUAL PATH ENDOSCOPE

(71) Applicant: VISIONSENSE LTD., Petach Tikva (IL)

(72) Inventor: Alex Chanin, Holland, PA (US)

(73) Assignee: VISIONSENSE LTD., Petach Tikva (IL)

( * ) Notice: Subject to any disclaimer, the term of this patent is extended or adjusted under 35 U.S.C. 154(b) by 98 days.

(21) Appl. No.: 15/499,363

(22) Filed: Apr. 27, 2017

(65) Prior Publication Data

US 2017/0318207 A1   Nov. 2, 2017

Related U.S. Application Data

(60) Provisional application No. 62/489,463, filed on Apr. 25, 2017, provisional application No. 62/330,282, filed on May 2, 2016.

(51) Int. Cl.
*A61B 1/00* (2006.01)
*H04N 5/225* (2006.01)
(Continued)

(52) U.S. Cl.
CPC ......... *H04N 5/2256* (2013.01); *A61B 1/0005* (2013.01); *A61B 1/00009* (2013.01); *A61B 1/00193* (2013.01); *A61B 1/043* (2013.01); *A61B 1/0638* (2013.01); *A61B 1/0646* (2013.01); *A61B 1/07* (2013.01); *G02B 5/208* (2013.01); *G02B 23/2415* (2013.01);
(Continued)

(58) Field of Classification Search
None
See application file for complete search history.

(56) References Cited

U.S. PATENT DOCUMENTS 5,749,830 A   5/1998   Kaneko et al.
6,471,642 B1   10/2002   Igarashi
(Continued)

OTHER PUBLICATIONS

Extended European Search Report dated Aug. 30, 2017 for European Application No. 17000751.2 (7 Pages).

*Primary Examiner* — Chikaodili E Anyikire
(74) *Attorney, Agent, or Firm* — Pearl Cohen Zedek Latzer Baratz LLP

(57) ABSTRACT

A novel dual-path-endoscope where a multi-function light source produces a first-light and a second-light toward an object. The first-light exhibits first-light-characteristics. The second-light exhibits second-light-characteristics different from the first-light-characteristics. The endoscope includes two light-paths, the disparity there between is larger than zero. Each light-path includes a respective pupil and a respective light-separator coupled with the pupil, transmitting there through one of the first-light and the second-light, associating the first-light and the second-light with a respective light-path. The dual-channel-imager includes two imaging sensors, each associated with a respective light-path and optically coupled with a respective light-separator. Each imaging-sensor exhibits sensitivity to the characteristics of the respective one of the first-light and the second-light. A first imaging-sensor acquires a first-image of the first-light reflected of the object and a second imaging-sensor acquires a second-image of the second-light reflected of the object. The processor processes the acquired images.

13 Claims, 6 Drawing Sheets

(51) Int. Cl.
*H04N 9/097* (2006.01)
*H04N 5/232* (2006.01)
*G02B 23/24* (2006.01)
*G02B 5/20* (2006.01)
*A61B 1/04* (2006.01)
*A61B 1/07* (2006.01)
*A61B 1/06* (2006.01)
*H04N 5/33* (2006.01)
*H04N 9/64* (2006.01)

(52) U.S. Cl.
CPC ..... *G02B 23/2461* (2013.01); *G02B 23/2484* (2013.01); *H04N 5/23293* (2013.01); *H04N 5/332* (2013.01); *H04N 9/097* (2013.01); *A61B 1/00165* (2013.01); *A61B 1/00167* (2013.01); *A61B 1/00186* (2013.01); *H04N 9/646* (2013.01); *H04N 2005/2255* (2013.01)

(56) References Cited

U.S. PATENT DOCUMENTS

| | | | |
|---|---|---|---|
| 7,405,877 | B1 | 7/2008 | Schechterman |
| 8,228,368 | B2* | 7/2012 | Zhao ............... A61B 1/00009 348/45 |
| 8,810,631 | B2 | 8/2014 | Scott et al. |
| 8,892,190 | B2 | 11/2014 | Docherty et al. |
| 9,798,131 | B2 | 10/2017 | Shechterman |
| 9,883,788 | B2 | 2/2018 | Shechterman |
| 2006/0293556 | A1* | 12/2006 | Garner ............... A61B 1/00009 600/101 |
| 2007/0182842 | A1* | 8/2007 | Sonnenschein .... A61B 1/00124 348/340 |
| 2009/0268010 | A1* | 10/2009 | Zhao ............... A61B 1/00009 348/45 |
| 2013/0041221 | A1* | 2/2013 | McDowall ......... A61B 1/00096 600/111 |
| 2014/0031659 | A1* | 1/2014 | Zhao .................... A61B 5/743 600/371 |

* cited by examiner

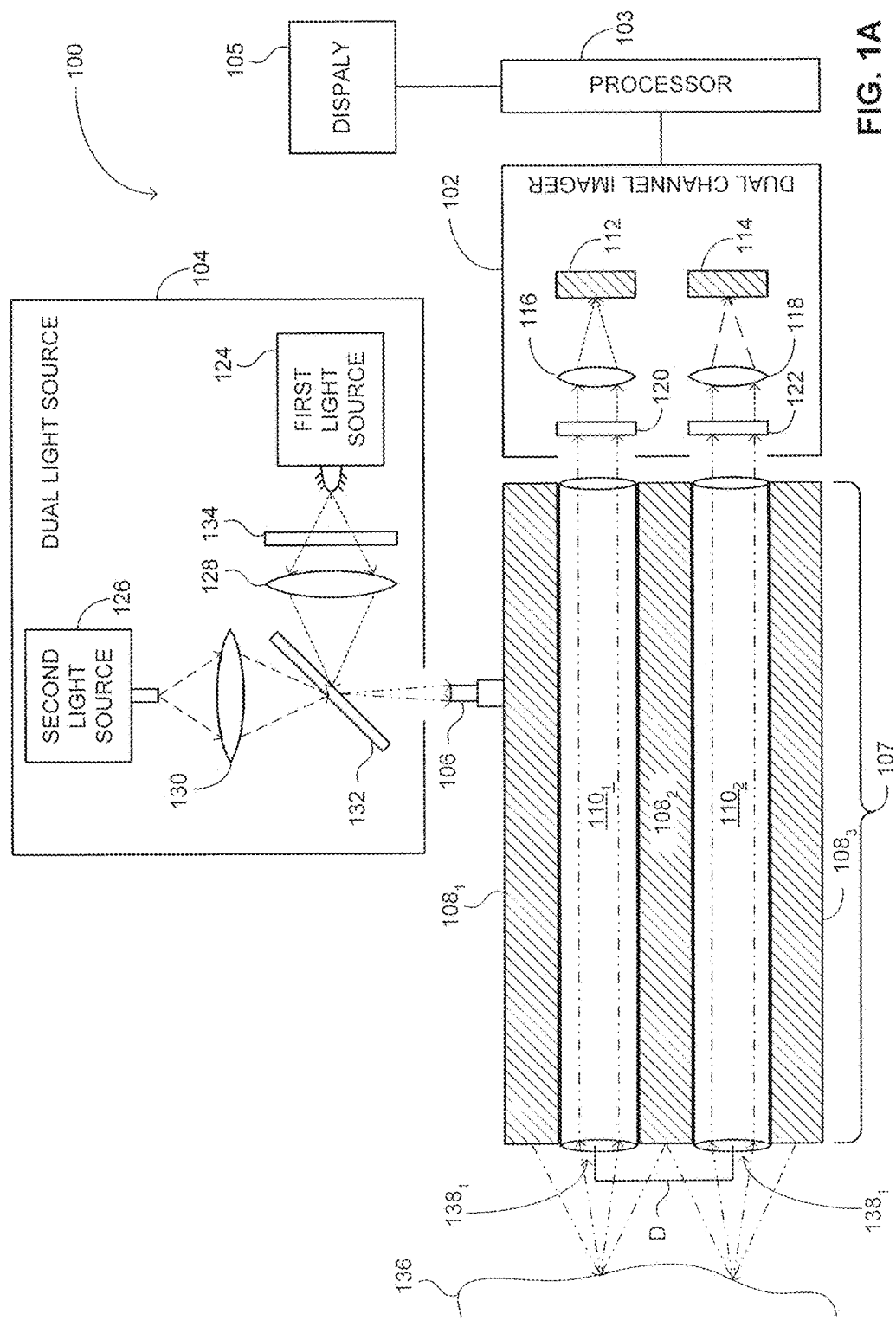

DUAL PATH ENDOSCOPE

CROSS-REFERENCE TO RELATED APPLICATIONS

This application claims the benefit of, and priority to, U.S. Provisional Application Ser. No. 62/330,282, filed May 2, 2016 and U.S. Provisional Application Ser. No. 62/489,463, filed Apr. 25, 2017, the contents of each of which are hereby incorporated by reference herein in their entireties.

FIELD

The disclosed technique relates to endoscopes in general, and to a dual path endoscope system with non-zero disparity between the two paths and methods therefor in particular.

BACKGROUND

A fluorescent endoscope is an imaging system for imaging blood flow, by imaging fluorescence radiation emitted by a fluorescence agent (e.g., a dye) illuminated by light generated by a fluorescent light source. Such an endoscope may be employed, for example, during surgery for visualizing the blood flow, and for evaluating tissue perfusion. In some cases, an additional visible light image of the observed area may be employed to provide anatomical reference to the fluorescent image.

In known in the art techniques in which both visible and fluorescent light are employed, the fluorescence image and white light image are acquired through the same channel of an endoscope (either in 3D or 2D imaging modes). In other words, two dissimilar imaging modalities are transmitted over the same channel of an endoscope. Although in such known in the art techniques the registration between the two images is simplified, the image acquisition is either interspersed in time (i.e., only white light image or fluorescent image are acquired at a time) or the white illumination is substantially attenuated to allow the relatively weaker fluorescence signal to be brighter than the background white light image.

U.S. Pat. No. 8,810,631 to Scott et al, entitled "Augmented stereoscopic visualization for a surgical robot using a captured visible image combined with a fluorescence image and a captured visible image" directs to an endoscope system which includes image capture system and a combination light source. The combination light source produces white light and at least one fluorescence excitation light. The imaging system captures light returned from tissue of a patient. According to one embodiment directed to by Scott et al, the imaging system includes 2 Charge Coupled Device (CCD) sensors. One CCD sensor captures an image of the white light only and the other CCD sensor captures an image of both white and fluorescent light. A processor processes the acquired images to generate a 3D stereoscopic image of both white light and fluorescent light.

SUMMARY

It is an object of the disclosed technique to provide a novel dual path endoscope system. The system includes a multi-function light source, an endoscope, a dual channel imager and a processor coupled with the dual channel imager. The multi-function light source produces a first light and a second light and directs the first light and the second light toward an object. The first light exhibits first light characteristics. The second light exhibits second light characteristics different from the first light characteristics. The endoscope includes two light paths, the disparity between the two light paths is larger than zero. Each light path at least includes a respective pupil and a respective light separator coupled with the pupil for transmitting there through a respective one of the first light and the second light, thereby associating the first light and the second light with a respective light path. The dual channel imager at least includes two imaging sensors. Each imaging sensor is associated with a respective one of the light paths. Each imaging sensor is optically coupled with the light separator associated with the respective light path. Each imaging sensor exhibits sensitivity to the characteristics of the respective one of the first light and the second light. A first one of the imaging sensors acquires a first image of the first light reflected of the object and a second one of the imaging sensors acquires a second image of the second light reflected of the object. The processor processes the acquired images

BRIEF DESCRIPTION OF THE DRAWINGS

The disclosed technique will be understood and appreciated more fully from the following detailed description taken in conjunction with the drawings in which:

FIG. 1A is a schematic illustration of a dual path endoscope system, constructed and operative in accordance with an embodiment of the disclosed technique;

DETAILED DESCRIPTION

The disclosed technique overcomes the disadvantages of the prior art by providing a dual path endoscope system with non-zero disparity between the two channels and methods therefor. Such a dual path endoscope includes a two-channel imager, which includes two image sensors. One sensor is sensitive to a first light exhibiting respective first light characteristics and the other sensor is sensitive to a second light exhibiting respective second light characteristics different from the first light characteristics. For example, the first light is visible light and the second light is Infrared (IR) light. Typically, a dual path endoscope system according to the disclosed technique is a fluorescent endoscope in which one path is a fluorescence path which employs a fluorescent light (e.g., a laser which excites a fluorescence agent such as a dye) for acquiring a fluorescent image. The other path is a visible light path for acquiring a visible light image. The two images may be displayed separately. The non-zero disparity may be accounted for by employing image processing to generate a 2D image or enables a combined 3D image from the two images. The non-zero disparity physically enables to employ two separate optical paths, thus allowing the visible light path to be independent of the fluorescence light path. The dual channel imager may be located in either distal end of the dual path endoscope or the proximal end of the dual path endo scope. An image sensor may be a single chip sensor containing an integrated color filter or a multi-chip sensor with prisms to separate colors according to wavelength.

Figure 1B:
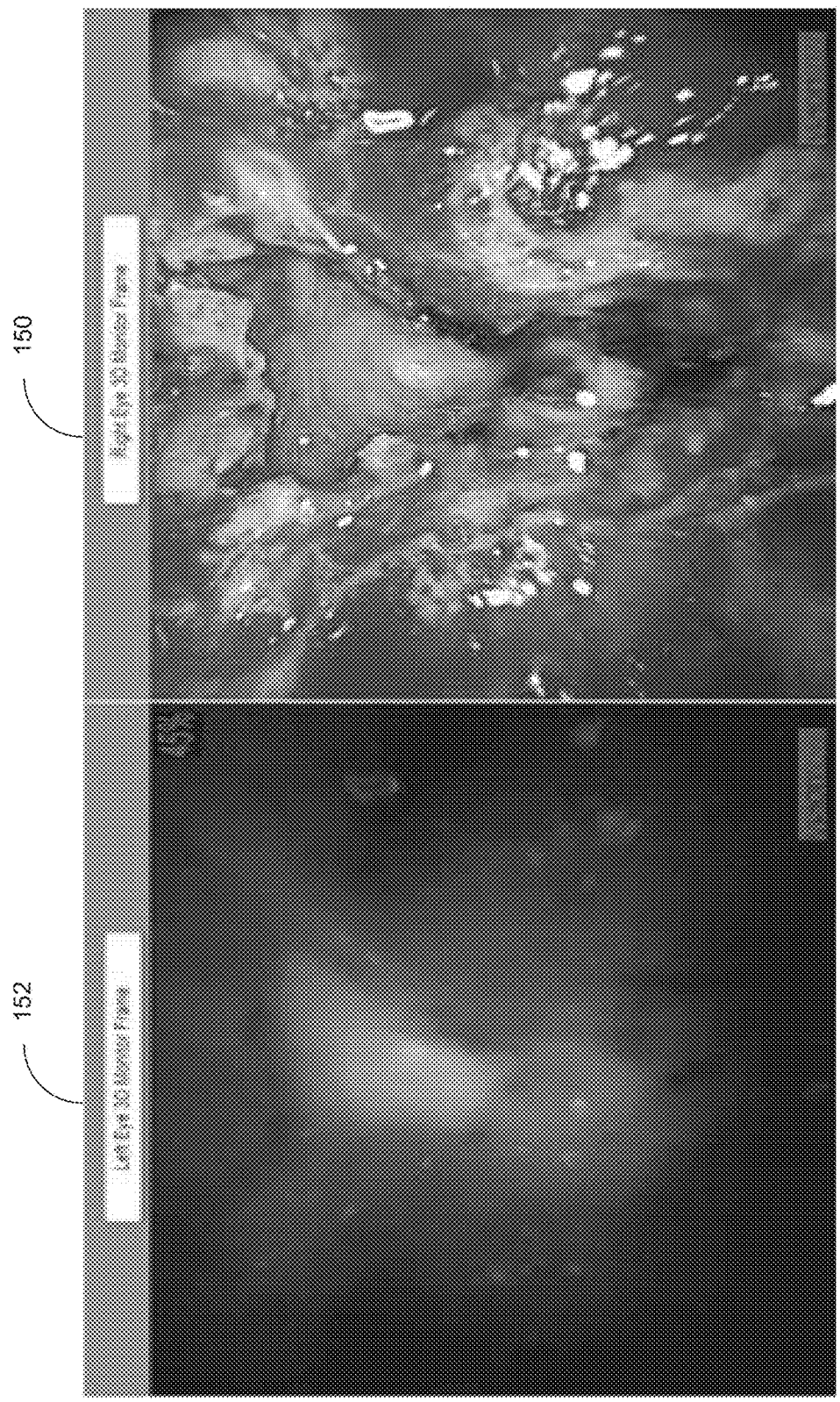
FIG. 1B is a schematic illustration of two images acquired with a dual path endoscope system such as depicted of FIG. 1A.
Figure 1C:
FIG. 1C is a schematic illustration of a combined image acquired with a dual path endoscope system such as depicted of FIG. 1A.

Reference is now made to FIGS. 1A, 1B and 1C. FIG. 1A is a schematic illustration of a dual path endoscope system, generally referenced 100, constructed and operative in accordance with an embodiment of the disclosed technique. FIG. 1B is a schematic illustration of two images, 150 and 152 acquired with a system such as endoscope system 100. FIG. 1C is a schematic illustration of a combined image 154 acquired with a system such as endoscope system 100.

With reference to FIG. 1A, endoscope system 100 includes a dual path imager 102, a multi-function light source 104, a processor 103, a display 105 and an endoscope 107. Endoscope 107 includes an optical terminal 106, optical fibers $108_1$, $108_2$ and $108_3$ and two optical channels, first optical channel $110_1$ and second optical channel $110_2$. Dual channel imager 102 is located at the proximal end of endoscope 107 and includes a first image sensor 112, a second image sensor 114, first imaging optics 116, second imaging optics 118, first light separator 120 and second light separator 122. Multi-function light source 104 includes a first light source 124 and a second light source 126, first light source optics 128, second light source optics 130 an optical combiner 132. Multi-function light source 104 optionally includes a short pass filter 134.

Processor 103 is coupled with display 105 and with dual channel imager 102. First imaging optics 116 is optically coupled with first imaging sensor 112 and with first light separator 120 and located therebetween. Second imaging optics 118 is optically coupled with first imaging sensor 114 and with first light separator 122 and located therebetween. First light separator 120 is optically coupled with first optical channel $110_1$ and second light separator 122 is optically coupled with second optical channel $110_2$. Entry pupil $138_1$, first optical channel $110_1$, first light separator 120 define a first light path. Entry pupil $138_1$, first optical channel $110_1$, first light separator 120, first imaging optics 116 and first imaging sensor 112 define a first image acquisition channel associated with the light generated by first light source 124. Entry pupil $138_2$, Second optical channel $110_2$, second light separator 122, define a second light path. Entry pupil $138_2$, Second optical channel $110_2$, second light separator 122, second imaging optics 118 and second imaging sensor 114 define a second image acquisition channel associated with the light generated by second light source 126. It is noted that the disparity 'D' between entry pupils $138_1$ and $138_2$ and thus between the two image acquisition channels is larger than zero (i.e., D>0). It is noted that the term 'image acquisition channel' and 'image acquisition path' are used herein interchangeably.

First light source optics 128 is optically coupled with first light source 124 and optical combiner 132 and located therebetween. Second light source optics 130 is optically coupled with second light source 126 and optical combiner 132 located therebetween. Optical combiner 132 is optically coupled with optical terminal 106. Optical terminal 106 is coupled with optical fibers $108_1$, $108_2$ and $108_3$.

The light generated by first light source 124 exhibits different distinguishable light characteristics (e.g., different wavelength, different polarization or different phase) from the light characteristics generated by second light source 126. The term 'distinguishable light characteristics' refers herein to characteristics by which the two lights may be distinguished therebetween, for example, with the aid of optical elements (e.g., filters) or with the aid of processing. First light source 124 is typically a white light source such as a Xenon light. When short pass filter 134 is included in multi-function light source 104, then short pass filter 134 attenuates light exhibiting wavelengths above a cutoff wavelength (e.g., above 700 nanometers). Second light source 126 is typically a fluorescence excitation light generated for example by a laser diode (e.g., at a wavelength of 805 nanometers). In FIG. 1A, light source 104 is depicted as including two light sources. However, in general, light source 104 may include more than two sources exhibiting distinguishable characteristics therebetween.

First imaging sensor 112 exhibits sensitivity in the wavelengths range of the light generated by first light source 124 and second imaging sensor exhibits sensitivity in the wavelengths range of the light generated by second light source. First imaging sensor 112 and second imaging sensors 124 are, for example CCD sensors or Complementary Metal Oxide Semiconductor (CMOS) sensor. First optical channel $110_1$ and second optical channel $110_2$ are position along endoscope 107 and may be constructed from an array of optical elements such lenses, rod lenses mirrors and the like.

First light source 124 projects the light generated thereby, indicated by a dotted line in FIG. 1A, toward first light optics 128. First light optics 128 focuses this light onto optical combiner 132. Second light source 126 projects the light generated thereby, indicated by a dashed line in FIG. 1A, toward second light optics 130. Second light optics 130 focuses this light onto optical combiner 132. Optical combiner 132 reflects the first light (i.e., generated by first light source 124) and transmits the second light (i.e., generated by second light source 126) to generate a combined light. The combined light, indicated by a dashed double dotted line in FIG. 1A, is then transmitted into optical fibers $108_1$, $108_2$ and $108_3$ by optical terminal 106. Optical fibers $108_1$, $108_2$ and $108_3$ transmit combined light through endoscope 107, which transmit the combined light onto object 136. Alternatively, light source 104 may direct the light generated by first light source 124 and the light generated by second lights source 126 separate from each other, through endoscope 107 (e.g., through separate light channels such as fiber optics) onto object 136. As a further alternative, light source 104 directs the combined light generated by first light source 124 and the light generated by second lights source 126 through endoscope 107 via one or more light channels onto object 136. In other words, endoscope 107 may include one or more light channels through which multi-function light source 104 may direct the light generated thereby.

Object 136 reflects the combined light toward two optical channels, first optical channel $110_1$ and second optical channel $110_2$ via respective entry pupils $138_1$ and $138_2$. Each one of first optical channel $110_1$ and second optical channel $110_2$ transmits the reflected combined light which entered thereto toward two channel imager 102. The light from first optical channel is transmitted through first light separator 120. First light separator 120 transmits only light which exhibits characteristics similar to the light generated by first light source 124 toward first imaging optics 116. First imaging optics 116 focuses this light onto first imaging sensor 112. Similarly, light separator 122 transmits only light which exhibits characteristics similar to the light generated by second light source 126 toward second imaging optics 118. Second imaging optics 118 focuses this light onto second imaging sensor 114. First imaging sensor 112 acquires a first image associated only with the first light and second imaging sensor 114 acquires a second image associated only with the second light. First imaging sensor 112 and second imaging sensor 114 provide the acquired images thereby to processor 103.

According to one alternative, processor 103 processes the acquired image separately (e.g., filtering) and provides each image to display 107 which display the images separately. With reference to FIG. 1B, image 150 is and exemplary image acquired by first imaging sensor 112 referred to herein also as 'right eye image'. Image 152 is an exemplary image acquired by second imaging sensor 114 referred to herein also as 'left eye image'. The light emitted by first light source 124 to generated image 150 is white light in the visible part of the spectrum. The light emitted by second light source 126 to generated image 152 is in the IR part of the spectrum.

According to another alternative, processor 103 processes the acquired images and combines the two acquired images into a single combined image. To generate a combined image from the right eye image and the left eye image, processor 103 determines the shift of the second image, relative to the first image, based on the disparity 'D'. Processor 103 then shifts the second image according to the determined shift and further normalizes the intensities and color of the two images. Processor 103 than combines the two images (e.g., by creating a pseudo-color overlay of the fluorescence image on the white light image) and provides the combined image to display 107 which displays the combined image. With reference to FIG. 1C, image 154 is an exemplary combined image.

Figure 2:
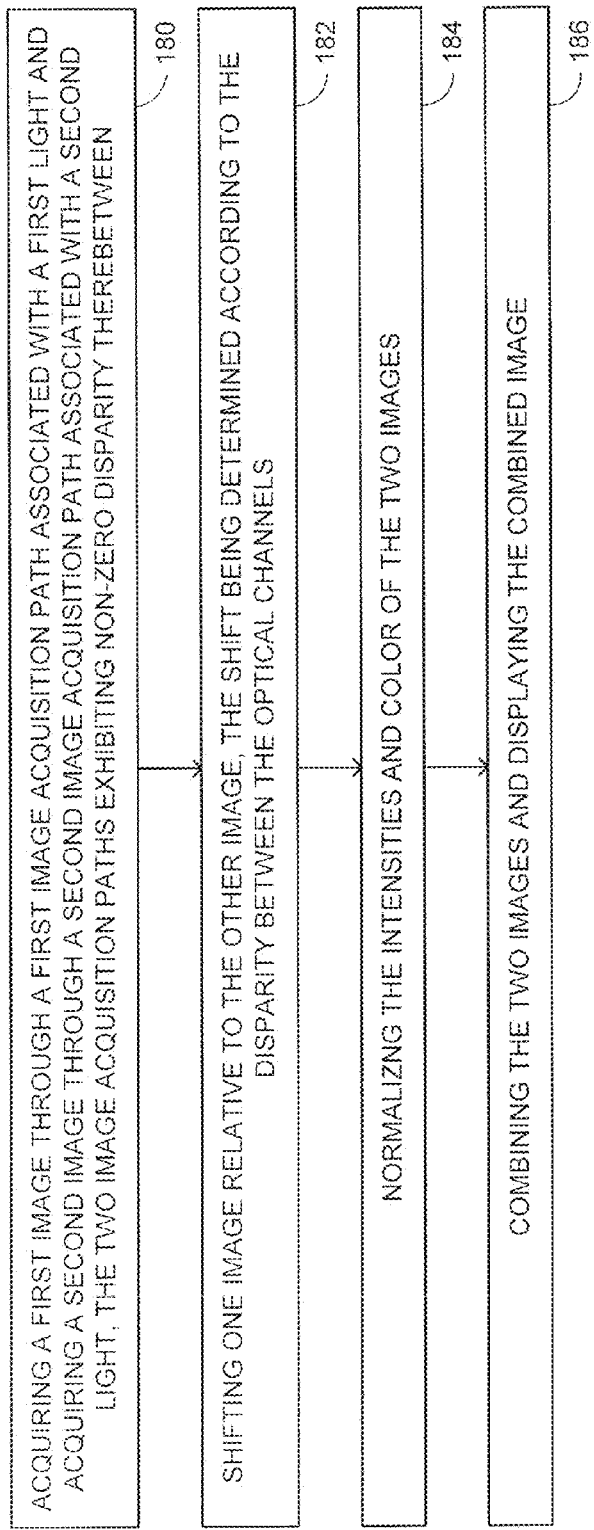
FIG. 2 is a schematic illustration of a method for combining two images acquired from two different image acquisition channels, operative in accordance with another embodiment of the disclosed technique.

Reference is now made to FIG. 2, which is a schematic illustration of a method for combining two images acquired from two different image acquisition paths, operative in accordance with another embodiment of the disclosed technique. In procedure 180, a first image is acquired through a first image acquisition path and a second image is acquired through a second image acquisition path. The first path is associated with a first light and the second path is associated with a second light. The image acquisition paths exhibiting non-zero disparity therebetween. With reference to FIG. 1A, first imaging sensor 112 acquires a first image through a first optical channel associated with the light generated by first light source 124. Second imaging sensor 114 acquires a second image through a first optical channel associated with the light generated by second light source 126.

In procedure 182, one image is shifted relative to the other image. The shift is determined according to the disparity between the optical channels. With reference to FIG. 1A, processor 103 determines the relative shift between the two acquired images and shifts one image relative to the other.

In procedure 184, intensities and color of the two images are normalized. With reference to FIG. 1A, processor 103 normalizes the intensities and the color of the two images.

In procedure 186, the two images are combined into a combined image and displayed. With reference to FIG. 1A, processor 103 combines the two images and provides the combined image to display 105 which displays the combined image.

In the embodiment described herein above in conjunction with FIG. 1A, optical channels $110_1$ and $110_2$ where physically separated. According to a further embodiment of the disclosed technique, the same optical channel may transmit the light associated with the two image acquisition paths. To that end two optical logical channels are defined within the single optical channel.

Figure 3:
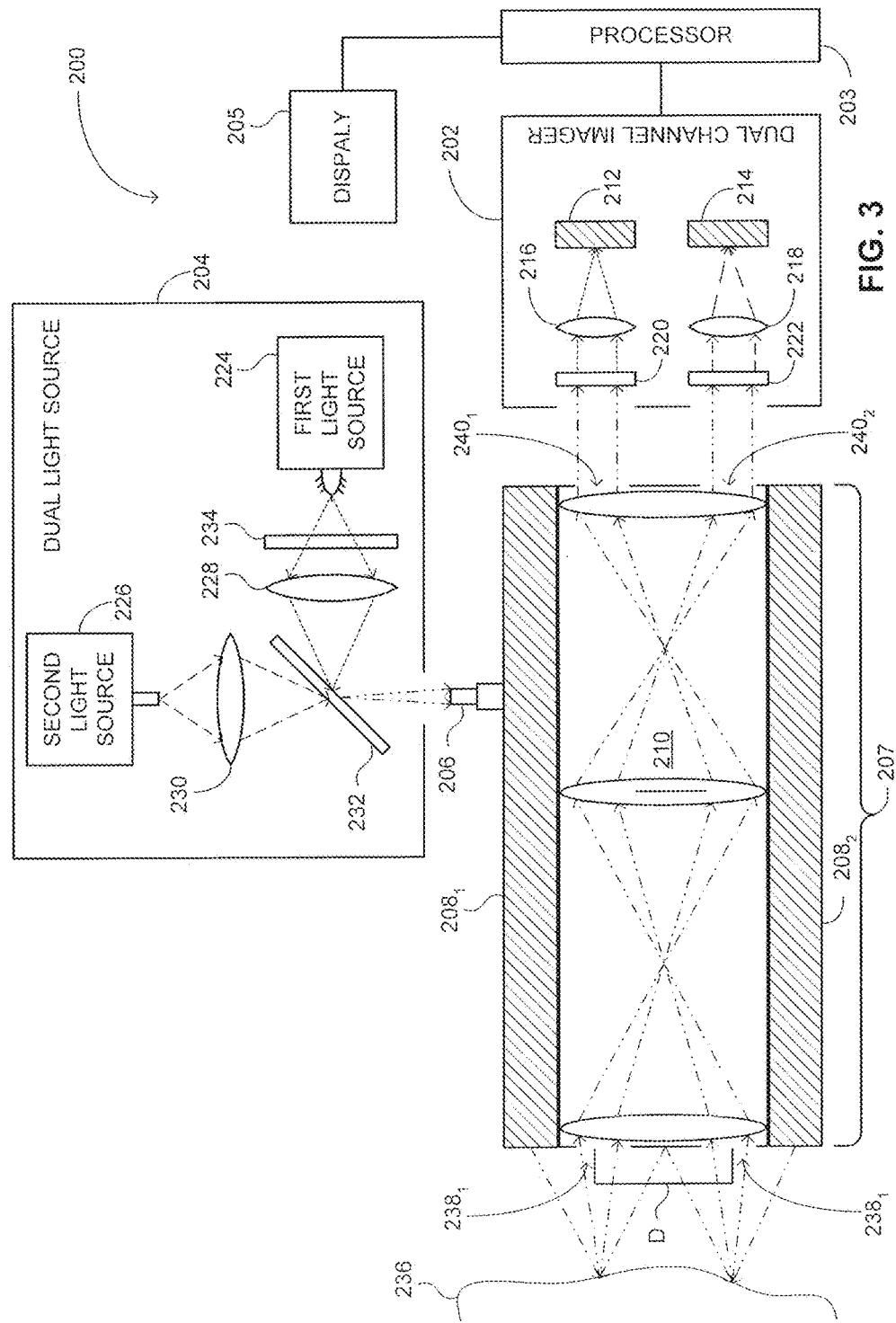
FIG. 3 is a schematic illustration of a dual paths endoscope system, constructed and operative in accordance with a further embodiment of the disclosed technique.

Reference is now made to FIG. 3, which is a schematic illustration of a dual path endoscope system, generally referenced 200, constructed and operative in accordance with a further embodiment of the disclosed technique. Endoscope system 200 includes a dual channel imager 202, a multi-function light source 204, a processor 203, a display 205 and an endoscope 207. Endoscope 207 includes an optical terminal 206, optical fibers $208_1$ and $208_2$ and an optical channel 210. Dual channel imager 202 is located at the proximal end of endoscope 207 and includes a first image sensor 222, a second image sensor 214, first imaging optics 216, second imaging optics 218, first light separator 220 and second light separator 222. Multi-function light source 204 includes a first light source 224 and a second light source 226, first light source optics 228, second light source optics 230 an optical combiner 232. Multi-function light source 204 optionally includes a short pass filter 234.

Processor 203 is coupled with display 205 and with dual channel imager 202. First imaging optics 216 is optically coupled with first imaging sensor 212 and with first light separator 220 and located therebetween. Second imaging optics 218 is optically coupled with first imaging sensor 214 and with first light separator 224 and located therebetween. First light separator 220 is optically coupled with optical channel 210 via second exit pupil $240_1$ and second light separator 222 is optically coupled with second optical channel 210 via second exit pupil $240_2$. Entry pupil $238_1$, optical channel 210, exit pupil $240_1$, first light separator 220 define a first light path with the light generated by first light source 224. Entry pupil $238_1$, optical channel 210, exit pupil $240_1$, first light separator 220, first imaging optics 216 and first imaging sensor 212 define a first image acquisition path associated with the light generated by first light source 224. Entry pupil $238_2$ optical channel 210, exit pupil $240_2$, second light separator 222, define a second light path associated with the light generated by second light source 226. Entry pupil $238_2$ optical channel 210, exit pupil $240_2$, second light separator 222, second imaging optics 218 and second imaging sensor 214 define a second image acquisition path associated with the light generated by second light source 226. It is noted that the disparity 'D' between entry pupils $238_1$ and $238_2$ and thus between the two image acquisition paths is larger than zero (i.e., D>0).

First light source optics 228 is optically coupled with first light source 224 and optical combiner 232 and located therebetween. Second light source optics 230 is optically coupled with second light source 226 and optical combiner 232 located therebetween. Optical combiner 232 is optically coupled with optical terminal 206. Optical terminal 206 is coupled with optical fibers $208_1$ and $208_2$.

Multi-function light source 204 is similar to multi-function light source 104 described above in conjunction with FIG. 1A. The light generated by first light source 224 exhibits different distinguishable characteristics (e.g., wavelength, polarization or phase) from the light generated by second light source 226. The term 'distinguishable characteristics' refers herein to characteristics by which the two lights may be distinguished therebetween, for example, with the aid of optical elements (e.g., filters) or with the aid of processing. First light source 224 is typically a white light source such as a Xenon light. When short pass filter 234 is included in multi-function light source 204, then short pass filter 234 attenuates light exhibiting wavelengths above a cutoff wavelength (e.g., above 700 nanometers). Second light source 226 is typically a fluorescence excitation light generated for example by a laser diode (e.g., at a wavelength of 805 nanometers). First imaging sensor 212 exhibits sensitivity in the wavelengths range of the light generated by first light source 224 and second imaging sensor exhibits sensitivity in the wavelengths range of the light generated by second light source. First imaging sensor 221 and second imaging sensors 224 are, for example CCD sensors or CMOS sensor (i.e., similar to first imaging sensor 112 and second imaging sensor 124—FIG. 1). Optical channel 210 may be constructed from an array of optical elements such lenses, rod lenses mirrors and the like (i.e., also similar to first optical channel $110_1$ and Second optical channel $110_2$—FIG. 1).

First light source 224 projects the light generated thereby, indicated by a dotted line in FIG. 2, toward first light optics 228. First light optics 228 focuses this light onto optical combiner 232. Second light source 226 projects the light generated thereby, indicated by a dashed line in FIG. 2, toward second light optics 230. Second light optics 230 focuses this light onto optical combiner 232. Optical combiner 232 reflects the first light (i.e., generated by first light source 224) and transmits the second light (i.e., generated by second light source 226) to generate a combined light. The combined light, indicated by a dashed doubled dotted line in FIG. 2, is then transmitted into optical fibers $208_1$ and $208_2$ by optical terminal 206. Optical fibers $208_1$ and $208_2$ transmit combined light through endoscope 207 and transmit the combined light onto object 236.

Object 236 reflects the combined light toward entry pupils $238_1$ and $238_2$ and thus into the optical channel 210. Optical channel 210 transmits the reflected combined light which entered through first entry pupil $238_1$ via a first optical path within optical channel 210. Similarly, optical channel 210 transmits the reflected combined light, which entered through second entry pupil $238_2$ via a second optical path within optical channel 210. The light from first optical path exits via first exit pupil $240_1$ and is transmitted through first light separator 220. The light from second optical path exits via second exit pupil $240_2$ and is transmitted through second light separator 222. First light separator 220 transmits only light which exhibits characteristics similar to the light generated by first light source 224 toward first imaging optics 216. First imaging optics 216 focuses this light onto first imaging sensor 212. Similarly, light separator 222 transmits only light which exhibits characteristics similar to the light generated by second light source 226 toward second imaging optics 218. Second imaging optics 218 focuses this light onto second imaging sensor 214. First imaging sensor 212 acquires a first image associated only with the first light and second imaging sensor 214 acquires a second image associated only with the second light. First imaging sensor 212 and second imaging sensor 214 provide the acquired images thereby to processor 203. Processor 203 processes the image to either display each image separately or combine the two image similar to as described above in conjunction with FIGS. 1A-1C.

Figure 4:
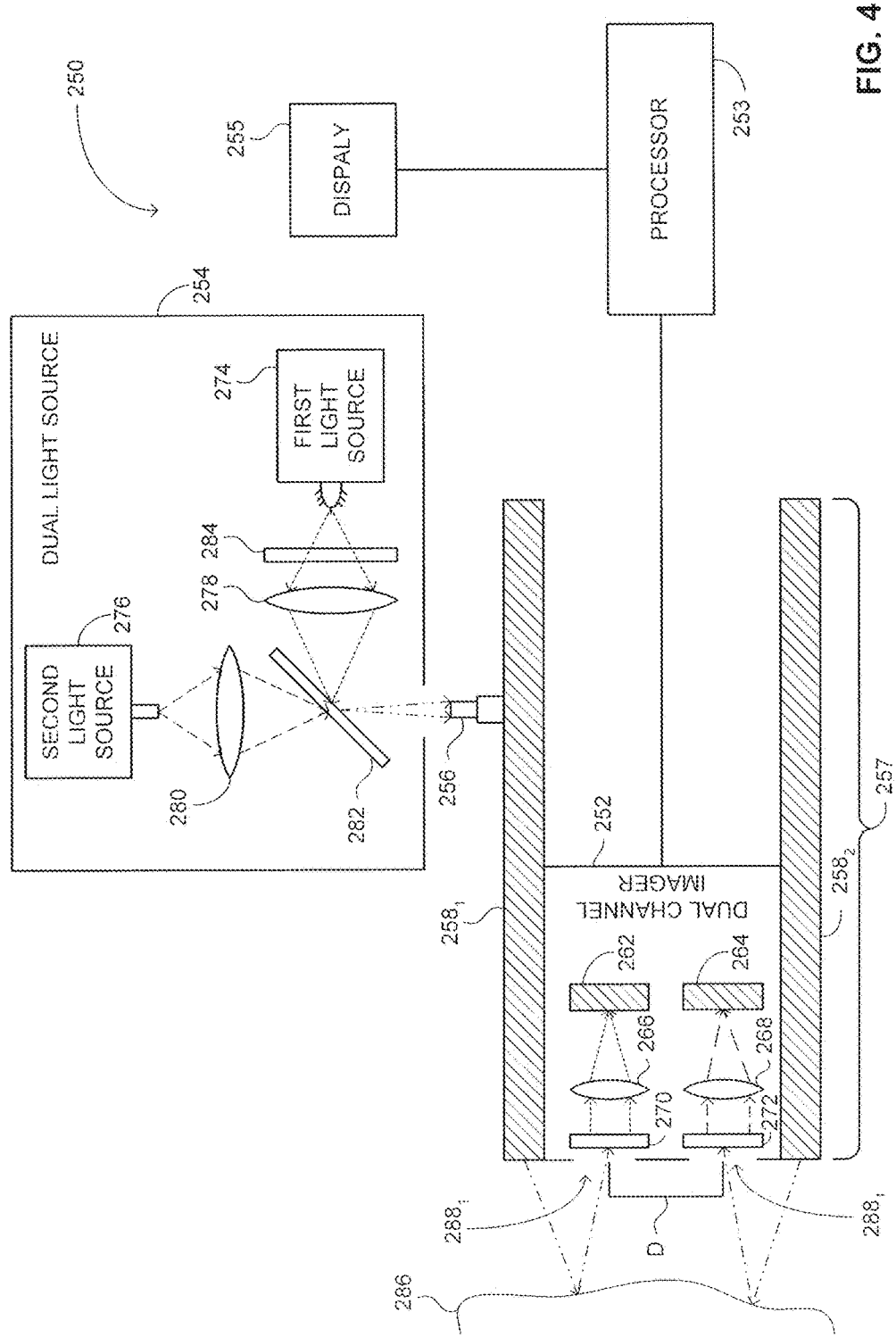
FIG. 4, is a schematic illustration of a dual path endoscope system, constructed and operative in accordance with another embodiment of the disclosed technique.

Reference is now made to FIG. 4, which is a schematic illustration of a dual paths endoscope system, generally referenced 250, constructed and operative in accordance with another embodiment of the disclosed technique. Endoscope system 250 includes a dual channel imager 252, a multi-function light source 254, a processor 253, a display 255 and an endoscope 257. Endoscope 257 includes an optical terminal 256, optical fibers $258_1$ and $258_2$. Dual channel imager 252 is located at the distal end of endoscope 250 and includes a first image sensor 272, a second image sensor 264, first imaging optics 266, second imaging optics 268, first light separator 270 and second light separator 272. Dual channel imager 252 may be embodied as a semiconductor chip located at the tip of endoscope 257. Multi-function light source 254 includes a first light source 274 and a second light source 276, first light source optics 278, second light source optics 280 an optical combiner 282. Multi-function light source 254 optionally includes a short pass filter 284.

Processor 253 is coupled with display 255 and with dual channel imager 252. First imaging optics 266 is optically coupled with first imaging sensor 262 and with first light separator 270 and located therebetween. Second imaging optics 268 is optically coupled with first imaging sensor 264 and with first light separator 274 and located therebetween. First light separator 270 entry pupil $288_1$ and second separator 272 is optically second entry pupil $288_2$. Entry pupil $288_1$, first light separator 270 define a first light path associated with the light generated by first light source 274. Entry pupil $288_1$, first light separator 270, first imaging optics 266 and first imaging sensor 262 define a first image acquisition path associated with the light generated by first light source 274. Entry pupil $288_2$, second light separator 272 define a second light path the light generated by second light source 276. Entry pupil $288_2$, second light separator 272, second imaging optics 268 and second imaging sensor 264 define a second image acquisition path associated with the light generated by second light source 276. It is noted that the disparity 'D' between entry pupils $288_1$ and $288_2$ and thus between the two image acquisition paths is larger than zero (i.e., D>0).

First light source optics 278 is optically coupled with first light source 274 and optical combiner 282 and located therebetween. Second light source optics 280 is optically coupled with second light source 276 and optical combiner 282 located therebetween. Optical combiner 282 is optically coupled with optical terminal 256. Optical terminal 256 is coupled with optical fibers $258_1$ and $258_2$.

Multi-function light source 254 is similar to multi-function light source 104 described above in conjunction with FIG. 1A. The light generated by first light source 274 exhibits different distinguishable characteristics (e.g., wavelength, polarization or phase) from the light generated by second light source 276. The term 'distinguishable characteristics' refers herein to characteristics by which the two lights may be distinguished therebetween, for example, with the aid of optical elements (e.g., filters) or with the aid of processing. First light source 274 is typically a white light source such as a Xenon light. When short pass filter 284 is included in multi-function light source 254, then short pass filter 284 attenuates light exhibiting wavelengths above a cutoff wavelength (e.g., above 700 nanometers). Second light source 276 is typically a fluorescence excitation light generated for example by a laser diode (e.g., at a wavelength of 805 nanometers). First imaging sensor 262 exhibits sensitivity in the wavelengths range of the light generated by first light source 274 and second imaging sensor exhibits sensitivity in the wavelengths range of the light generated by second light source. First imaging sensor 262 and second imaging sensors 274 are, for example CCD sensors or CMOS sensor (i.e., similar to first imaging sensor 112 and second imaging sensor 124—FIG. 1). Optical channel 260 may be constructed from an array of optical elements such lenses, rod lenses mirrors and the like (i.e., also similar to first optical channel $110_1$ and Second optical channel $110_2$—FIG. 1).

First light source 274 projects the light generated thereby, indicated by a dotted line in FIG. 2, toward first light optics 278. First light optics 278 focuses this light onto optical combiner 282. Second light source 276 projects the light generated thereby, indicated by a dashed line in FIG. 2, toward second light optics 280. Second light optics 280 focuses this light onto optical combiner 282. Optical combiner 282 reflects the first light (i.e., generated by first light source 274) and transmits the second light (i.e., generated by second light source 276) to generate a combined light. The combined light, indicated by a dashed doubled dotted line in FIG. 2, is then transmitted into optical fibers $258_1$ and $258_2$ by optical terminal 256. Optical fibers $258_1$ and $258_2$ transmit combined light through endoscope 257 and transmit the combined light onto object 286.

Object 286 reflects the combined light toward entry pupils $288_1$ and $288_2$ and thus into the two image acquisition paths. The light passing through entry pupil $288_1$ is transmitted through first light separator 270. The light passing through entry pupil $288_2$ is transmitted through second light separator 272. First light separator 270 transmits only light which exhibits characteristics similar to the light generated by first light source 274 toward first imaging optics 266. First imaging optics 266 focuses this light onto first imaging sensor 262. Similarly, light separator 272 transmits only light which exhibits characteristics similar to the light generated by second light source 276 toward second imaging optics 268. Second imaging optics 268 focuses this light onto second imaging sensor 264. First imaging sensor 262 acquires a first image associated only with the first light and second imaging sensor 264 acquires a second image associated only with the second light. First imaging sensor 262 and second imaging sensor 264 provide the acquired images thereby to processor 253. Processor 253 processes the image to either display each image separately or combine the two image similar to as described above in conjunction with FIGS. 1A-1C.

It will be appreciated by persons skilled in the art that the disclosed techniques are not limited to what has been particularly shown and described hereinabove. Rather, the scope of the disclosed techniques are defined only by the claims, which follow.

The invention claimed is:

1. A dual path endoscope system comprising:
a multi-function light source producing a first light and a second light and directing said first light and said second light toward an object, said first light exhibiting first light characteristics, said second light exhibiting second light characteristics different from said first light characteristics;
a single endoscope including two light paths within the single endoscope, and within a single optical channel, the disparity between said two light paths being larger than zero, each light path at least comprising:
a respective entry pupil;
a respective exit pupil;
and
a respective light separator optically coupled with said entry pupil for transmitting there through a respective one of said first light and said second light, thereby associating said first light and said second light with a respective light path;
a dual channel imager at least including two imaging sensors, each imaging sensor being associated with a respective one of said light paths, each imaging sensor being optically coupled with the light separator associated with the respective light path, each imaging sensor exhibiting sensitivity to the characteristics of said respective one of said first light and said second light, a first one of said imaging sensors acquires a first image of said first light reflected of said object and a second one of said imaging sensors acquires a second image of said second light reflected of said object; and
a processor, coupled with said dual channel imager for processing said acquired images.

2. The system according to claim 1, wherein said dual channel imager is located at the proximal end said endoscope.

3. The system according to claim 2, wherein said endoscope further comprises: an optical terminal for receiving light from said multi-function light source; and at least one optical fiber, coupled with said optical terminal for transmitting said light through said endoscope.

4. The system according to claim 1, wherein said dual channel imager is located at the distal end of said endoscope.

5. The system according to claim 1, wherein said first light characteristics and said second light characteristics are selected from the group consisting of wavelength, polarization, and phase.

6. The system according to claim 1, wherein said processor processes said first image and said second image, separately.

7. The system according to claim 1, wherein said processor processes said first image and said second image and combines said first image and said second image into a single combined image by determining the shift of one of said first image and said second image relative to the other image based on said disparity and shifting said other image according to the determined shift and combining said first image and said second image.

8. The system according to claim 7, wherein said processor further normalizes the intensities and color of said first image and said second image.

9. The system according to claim 7, wherein said processor combines the two acquired images by creating a pseudo-color overlay of said second image over said first image.

10. The system according to claim 1, further including a display for displaying at least one image provided by said processor.

11. The system according to claim 1, wherein said multi-function light source includes a first light source generating said first light and a second light source generating said second light.

12. The system according to claim 11, wherein said multi-function light source further comprises: a first light source optics optically coupled with said first light source; a second light source optics optically coupled with said first light source; and an optical combiner optically coupled with said first light source optics and with said second light source optics for generating a combined light from said first light and said second light and directing said combined light toward said object.

13. The system according to claim 11, wherein said multi-function light source further comprises a short pass filter optically coupled with said first light source and with said first light source optics for attenuating light exhibiting wavelengths above a cutoff wavelength.

* * * * *